United States Patent [19]

Studholme et al.

[11] Patent Number: 5,323,008
[45] Date of Patent: Jun. 21, 1994

[54] FLUOROMETER DETECTION SYSTEM

[75] Inventors: Robert M. Studholme, Saratoga; David A. Blau, Cupertino, both of Calif.

[73] Assignee: Diatron Corporation, San Diego, Calif.

[21] Appl. No.: 855,238

[22] Filed: Mar. 23, 1992

[51] Int. Cl.⁵ .................................................. G01N 21/64
[52] U.S. Cl. ................................. 250/458.1; 250/459.1
[58] Field of Search ............... 250/458.1, 459.1, 461.1, 250/461.2; 356/318, 317, 417

[56] References Cited

U.S. PATENT DOCUMENTS

| | | | |
|---|---|---|---|
| 4,058,732 | 11/1977 | Wieder | 250/461.1 |
| 4,198,567 | 4/1980 | Eneroth et al. | 250/459.1 |
| 4,855,930 | 8/1989 | Chao et al. | 356/318 |
| 4,857,735 | 8/1989 | Noller | 250/343 |
| 4,877,965 | 10/1989 | Dandliker et al. | 250/458.1 |
| 4,895,156 | 1/1990 | Schulze | 250/458.1 |
| 5,071,249 | 12/1991 | Takahashi et al. | 250/458.1 |
| 5,196,709 | 3/1993 | Berndt et al. | 250/458.1 |

OTHER PUBLICATIONS

Meyer et al, "Polymere mit dem Zentralatom eines Makrocyclus in der Hauptkette", Die Angewandte Makromolekulare Chemie, 72, pp. 173-184, 1978 & Chem. Ab., 90 (14), 90:104387f, p. 1, Apr. 2, 1979.
Hartmann et al., "Polymere mit dem Zentralatom eines Makrocyclus in der Hauptkette,2", Die Makromolekulare Chemie, 176, pp. 831-847, 1975 & Chem. Ab., 83, p.4, 1975, 79670p.

*Primary Examiner*—Carolyn E. Fields
*Attorney, Agent, or Firm*—Lyon & Lyon

[57] ABSTRACT

An improved fluorescence detection system is provided which utilizes a relatively high powered, relatively high repetition rate light source with high speed detection electronics to increase system sensitivity and accuracy. In the preferred embodiments, a laser diode is the light source. In one embodiment, the position of a time window is varied to compile a decay profile of a fluorophore. In another embodiment, the time to detection of a photon is used to compile the decay profile. In one aspect of this invention, a histogram of the fluorescence decay is generated by determining a preliminary histogram of the shape and multiplying it by the ratio of the total number of events divided by the number of events comprising the preliminary histogram. In another aspect of this invention, the time of detection after excitation of the photon is started from a random time, such as after a preceding event is detected and the data stored.

32 Claims, 16 Drawing Sheets

FLUOROMETER DETECTION SYSTEM

FIELD OF THE INVENTION

This invention relates to detection of fluorescence from a solution or a surface. More particularly, this invention is adapted for measurement of transient state immuneassays.

BACKGROUND OF THE INVENTION

Fluorescence is the process of monitoring fluorescent radiation from an object for analysis, characterization or imaging. Typically, an excitation pulse of radiation is directed onto or into a sample, followed by fluorescence of the sample, and the detection of the fluorescent radiation. The detected fluorescence is used for sample analysis, characterization or imaging. In the case of an immuneassay, analysis of a sample is typically done by marking a desired species with a fluorescable tag, exciting the sample and monitoring for fluorescence from the tag.

Theoretically, fluorometry is capable of being the most sensitive of all analytic tools. It is possible to detect single photon events, and possible to re-excite a fluorophore and confirm the analysis. However, the problem which has plagued fluorescence has been in discriminating the fluorescent signal of interest from the background radiation in the system. Often times, the signal from "background" radiation may be 10,000 times larger than the intensity of the fluorescent signal of interest. Detection of the unwanted background radiation reduces the image quality and accuracy of the detection.

The problem caused by background radiation is particularly acute in biological systems. For example, in the analysis of blood plasma, the presence of a naturally occurring fluorescable material, such as biliverdin, causes substantial background radiation. Other sources of undesirable background radiation include ambient radiation, radiation from fast fluorescing materials (generally considered to be those with decay half lives on the order of 1 to 1.5 nanoseconds) and various scattering mechanisms, such as Raman scattering bands.

Earlier attempts to overcome the problem of background radiation have met with limited success. A first technique involves discriminating against background radiation on the basis of wavelength. Generally, a filter is used to reject detected radiation at all but a narrowly defined wavelength band. This technique has been less than successful principally because the background radiation may also be at the same wavelength as the desired fluorescence signal, and accordingly, still be passed through the filter and detected.

A second technique attempting to discriminate the desired fluorescent signal from the background is the so called time gating approach. Here, the fluorescent signal is observed in a short time window after the excitation. The time window may be varied both in its length and in its starting time. Through the use of the variable time window, the detected radiation may be observed at the maximal time for detection sensitivity- Historically, this technique has used a fluorophore of very long decay time (such as 1,000 nanoseconds) to allow the background fluorescence to substantially decay before detection of the fluorescent signal of interest. Generally however, long decay time fluorophores are less desirable than shorter decay time fluorophores because they are relatively insensitive and require longer times for overall analysis.

Historically, there have been two excitation pulse formats for transient state fluorescent analysis. One format utilizes a single, relatively high power pulse which excites the fluorophore. The transient state is typically monitored by a high speed photomultiplier tube by monitoring the analog signal representative of current as a function of time. Single pulse systems require sufficiently high power to excite a large number of fluorescent molecules to make detection reliable. The other principal format for transient state fluorescent analysis utilizes repetitive excitation pulses. Ordinarily, pulses of relatively short, typically nanosecond duration, light with power in the microwatt range are repetitively supplied to the sample at rates varying from 1 to 10,000 Hz. Ordinarily, the excitation source is a lamp, such as a Xenon-lamp. Frequently, the decay curve is measured digitally by determining the time to receipt of a photon. One commercially available system uses repetitive pulses (such as at 5,000 Hz) and strobes the photomultiplier tube at increasingly longer times after the flash in order to obtain a time dependent intensity signal. Detection in such systems has proved to be very time consuming and insensitive. A single analysis can take on the order of one hour, even at relatively high fluorescable dye concentrations (e.g. $10^{-6}$M).

Recently, significant advances have been made in the area of fluorescable dyes. In one aspect, dyes being excitable by longer wavelength radiation, such as in the red and infrared wavelengths, are now available. Applicant incorporates by reference the applications by Arrhenius, U.S. patent application Ser. No. 701,449, filed May 15, 1991, entitled, "Fluorescent Marker Components and Fluorescent Probes," (which is a continuation-in-part of U.S. patent application Ser. No. 523,601, filed May 15, 1990), and Dandliker and Hsu, U.S. patent application Ser. No. 701,465, filed May 15, 1991 entitled "Fluorescent Dyes Free of Aggregation and Serum Binding" (which is a continuation-in-part of U.S. patent application Ser. No. 524,212, filed May 15, 1990). Significant improvements in sensitivity are achieved through use of these modern dyes over older dyes.

Further significant advancements have been made in increasing sensitivity through data collection and analysis techniques. As disclosed in Dandliker et al., U.S. Pat. No. 4,877,965, entitled "Fluorometer," time gating techniques are used in conjunction with data collection and analysis techniques to obtain an improved signal relative to the background. Generally, Dandliker et al., considers the detected intensity as a function of time to be composed of signals from various sources, including the desired signal source, and various undesired background sources. Optimization of the desired signal is achieved through data collection and analysis techniques.

Further significant advancements have been made in the ability to measure relevant materials in immunoassays. For example, in Dandliker et al, U.S. patent application Ser. No. 490,770, filed Mar. 6, 1990, entitled "Transient State Luminescence Assays," (which is a continuation-in-part of U.S. patent application Ser. No. 365,420, filed Jun. 13, 1989) incorporated herein by reference, the bound and free form of materials in a homogeneous assay may be determined. Generally, the technique requires measurement of the time dependent decay of the intensity of parallel and perpendicular polarization components. By measuring the time dependent decay of various polarization states, it is possible to determine the bound and free forms of materials such as haptens, peptides, or small proteins in a homogeneous analysis format. Significantly, no separation of the bound and free materials is required.

Despite the significant and promising improvements made in the field of fluorescable dyes, and in the data analysis aspects, the actual methods and apparatus for achieving and detecting fluorescence have heretofore remained relatively unchanged. Utilizing even the most sensitive and best equipment, analysis can take an hour or more, even at high concentrations of materials. When fluorometry is used for immunoassay in a clinical context, time for analysis and proper diagnosis can be absolutely critical. Patient survival can depend on accurate, timely analysis. Additionally, rapid testing would permit retests of patients without having them wait significant periods of time, resulting in more rapid and accurate diagnosis. As to sensitivity, it is extremely desirable to be able to detect minute amounts of fluorescable material. However, as the amount of fluorescable material in a sample decreases, the ratio of the size of the undesired background signal to the desired signal increases. Further, since the time for analysis depends on the amount of fluorescent radiation received from the detector, low concentrations generally require substantially more time to analyze.

Heretofore, the time required for analysis has been prohibitively high. Known methods and apparatus have failed to provide rapid and accurate diagnosis and analysis of samples. This has been so despite the clear and known desirability of the use of fluorometry.

SUMMARY OF THE INVENTION

An improved fluorescence detection system utilizes a relatively high powered, relatively high repetition rate light source with high speed detection electronics to increase system sensitivity and accuracy. Preferably, the light source is a laser diode. High speed detection electronics permit single event photon counting.

In one embodiment, a light source, preferably a laser diode, is used to obtain the decayed end profile of a fluorophore by varying a position of a time window. Transient state detection is accomplished by repetitively exciting the fluorophore, and monitoring the number of events received by the detector within a defined time window. Laser diodes are beneficially used as they have relatively high power (such as 5 to 100 milliwatts), long lifetimes and may be pulsed at relatively high repetition rates (such as 10 MHz). The combination of relatively high power excitation pulses plus relatively high repetition rates results in substantially quicker and more accurate fluorescent measurements.

In a preferred embodiment, a high powered light source, preferably a laser diode, is used to obtain the decay profile of a fluorophore by measuring the time to receipt of a photon, and compiling a histogram from that data. A hardware counter determines the total number of detection events within a monitor time. The shape of the fluorescence decay curve is determined by generating a histogram of time of receipt of photons. In the preferred embodiment, a ramp voltage is sampled at time of event detection, and the voltage stored to compile a histogram. Once the preceding event is detected and the data stored, monitoring is resumed for detection of the next event. After the shape of the decay curve is determined, the correct intensity may be determined by multiplication of the ratio of total number of events detected divided by the total number of events comprising the histogram. Preferably, the dark current is determined and subtracted from the total count and histogram count before the ratio is determined. This technique permits direct generation of a histogram for which the data analysis techniques of Dandliker et al., U.S. Pat. No. 4,877,965 are directly applicable.

In another aspect of this invention, improved sensitivity is achieved by ignoring the data received immediately after the excitation pulse. In one embodiment, the data acquisition window is set to start at a time after the initial transient events are concluded. In another embodiment, the data is acquired but not used during data analysis.

Accordingly, it is a principal object of this invention to provide an improved fluorometer with greatly enhanced sensitivity. It is yet another object of this invention to provide a fluorometer capable of generating rapid and accurate determinations, often within a matter of seconds.

It is yet a further object of this invention to provide a system capable of measuring extremely low concentrations of fluorescable material.

It is an object of this invention to provide a fluorometer useful for the clinical setting in that it is relatively compact, of relatively low cost and relatively rugged.

It is a further object of this invention to provide a fluorometer particularly adapted to exploit the new generation, longer wavelength fluorescable dyes.

DETAILED DESCRIPTION

Figure 1:
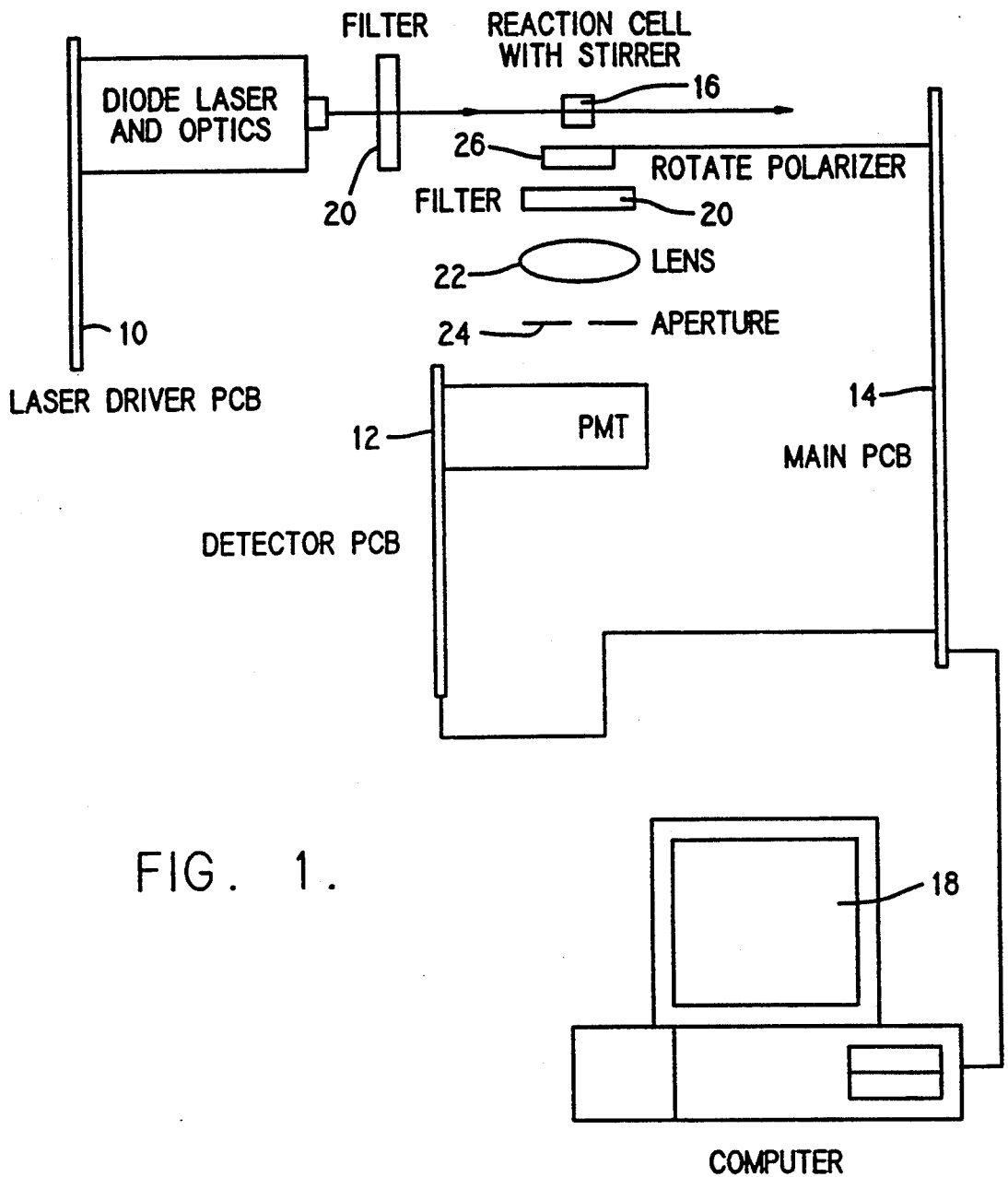
FIG. 1 shows an overview of the time gating transient state fluorescence decay measurement system.

In accordance with this invention, the intensity of fluorescence as a function of time may be quickly and accurately determined. The system may measure either total intensity as a function of time, or may be configured to measure the intensity of the various polarization components of the signal as a function of time. Further, both steady state and transient state analysis is possible. However, in the preferred embodiment, transient state fluorescence is monitored in preference to steady state fluorescence. Transient state fluorescence measurements tend to reduce the contribution from scatter bands and from fast fluorescers.

Broadly speaking, the systems of this invention comprise a source of excitation radiation to be directed onto or into a sample, and a detection system for measuring fluorescence from the sample. Conventional optics, such as filters and polarizers may be used in conjunction with the system of this invention as is well known to those skilled in the art.

The source of excitation radiation is characterized by being relatively high power and capable of operating at relatively high repetition rates. A laser diode meets both of these requirements. Generally, conventional laser diodes are available with power up to the 100 milliwatt range, which is roughly 1,000 times more powerful than conventional flash lamp fluorometers. It is expected that the power level of such devices will continue to increase. Further, conventional laser diodes may easily operate at 10 MHz range or higher, providing an over 1,000 times increase in the repetition rate as compared to flash lamp system and laser systems. Currently, laser diodes are available in any number of discrete output wavelengths which are compatible with commercially available fluorescent dyes. For example, laser diodes having wavelengths of 670 nm, 685 nm, 720 nm, 750 nm and 780 nm are available. Fluorescable dyes in these ranges may be manufactured in accordance with the teachings provided in the application to Arrhenius and Dandliker and Hsu, incorporated by reference above, and in Fluorescence Immunoassays Using Fluorescent Dyes Free of Aggregation and Serum Binding, filed on the same day as the instant application, and incorporated herein by reference. These dyes are generally referred to as caged dicarboxy silicon phthalocyane and when a digoxin probe is used, it is referred to as caged dicarboxy silicon phthalocyanine digoxigenin. Further, it is possible to overdrive the laser diodes in order to increase their power output, provided that they are not overheated to cause damage to the diode. Further, tunable laser diodes may be used in conjunction with this invention. For example, quantum well diodes provide the capability of tuning the output wavelength.

The detection system generally permits the detection of single photon events. High bandwidth devices are commercially available and are utilized to monitor detected events. The particular embodiments described below have been found to be particularly advantageous in connection with the detection methods described herein. Significantly, ultra high-speed events may be measured with detection electronics of significantly lower operating speed.

An important aspect of this invention is to perform fluorescent determinations on samples which are relatively unaffected by background events. Significant improvement in detection of desired fluorescence signal may be achieved by excluding the extremely transitory events from consideration. As detailed in the Experimental Results section, below, an improvement of approximately 100 times over conventional methods is achieved. This exclusion may be achieved in any number of ways. The data may be excluded by the time gating technique, for example, by setting the time gate to begin after the extremely transitory events are substantially concluded. Alternatively, the data may be collected but not considered during the analysis of the data. Further, the polarization of the radiation may be monitored, thereby permitting data analysis. Significant improvements in the sensitivity of the system may be achieved through this technique.

Overall, significant improvements in speed of analysis and sensitivity are achieved by the systems of this invention. By increasing the repetition rate and the power of the excitation pulses each by a factor of approximately 1,000, substantial improvements are made in detection sensitivity and drastically reduce the time for analysis. Detection may be done in a matter of seconds which previously would take hours. Further, use of fast detection electronics permits counting of single photon events, yet further increasing the sensitivity and accuracy of the system.

FIG. 1 shows an overview of one embodiment of this invention. The decay profile of the fluorophore is obtained by varying a time window, either or both as to its starting time or as to its duration. Structurally, the main components comprise an excitation source, a sample holder, related optics, and a detector. Optional processing and display capabilities are provided, for example, by a computer.

In the preferred embodiment, there are three main printed circuit boards, the laser driver PCB 10, the detector PCB 12, and the main PCB 14. The laser driver PCB 10 contains, preferably, the laser diode and certain optics. The laser driver PCB 10 is preferably rotatable such that the polarization orientation of the diode laser may be varied. The laser diode (not shown) on the laser driver PCB 10 is directed to the reaction cell 16 to cause excitation of the material contained within the reaction cell 16. The fluorescent radiation is detected by the detector PCB 12. Preferably, the detector is oriented at right angles from the input radiation. The main PCB 14 connects to the laser driver PCB 10 and detector PCB 12, plus communication with the computer 18. Optionally, optics may be placed within the path of the light, such as filters 20, lens 22, and/or aperture 24. Various combinations of polarizers may be utilized, as is well known to those skilled in the art, including rotatable polarizers 26 which is controlled both from the main PCB 14. Optionally, the reaction cell 16 may be provided with a stirrer, most preferably a magnetic type stirrer.

The computer 18 provides one way in which the user may interface with the system for control, processing, and display functions. The computer 18 may be either of a stand-alone type, or its necessary functions may be implemented with a collection of discreet components as is known to those skilled in the art. The computer 18 is FIG. 1 is shown with a characteristic display of a transient state decay of a fluorophore as a function of time. While the computer 18 may control numerous functions, it provides control for functions such as: laser on-time, laser power, laser on-off control, PMT high voltage set point, PMT current detection threshold set point, PMT on-off, delay to start of detection window, delay to end of detection window, number of cycles per experiment, polarizer parallel-perpendicular, stirrer on-off, and laser diode operating temperature.

Figure 2:
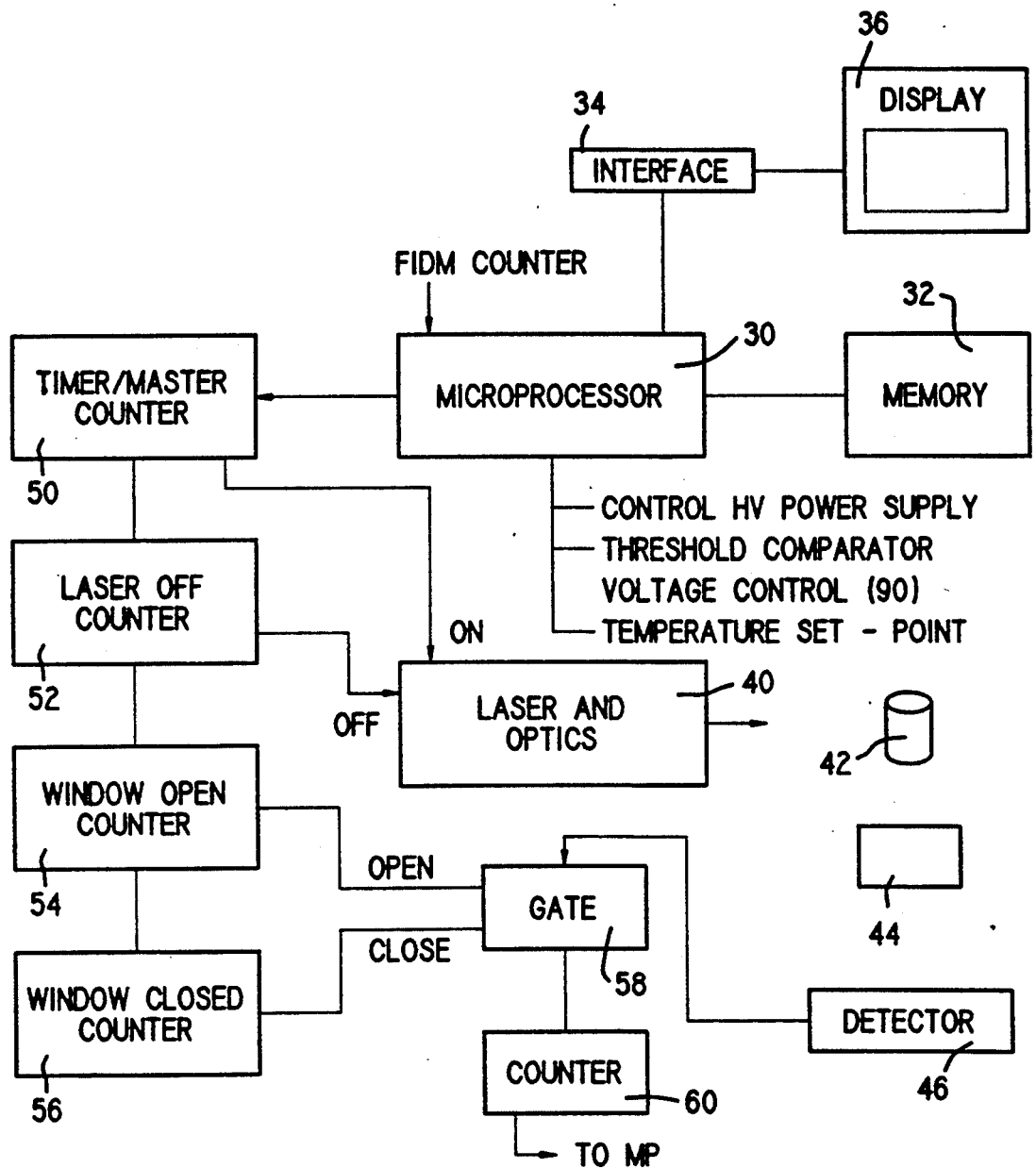
FIG. 2 shows a block diagram of the time gating system.

FIG. 2 shows a detailed block diagram of the main PCB 14. A microprocessor 30 controls operation of the board. In a preferred embodiment, a microprocessor 30 is an 80C32 processor and the memory 32 is 32K bytes of ROM and 32K bytes of RAM. Optionally, an interface 34, such as an RS232 port, permits connection to a computer for display 36. While not shown directly, the microprocessor 30 provides control signals for the high voltage power supply control, the threshold comparator voltage control, and the polarizer motor. The polarizer motor (not shown) serves to rotate the polarizer to permit detection of various polarization orientations.

The excitation source is provided by the laser and optics block 40. Excitation light irradiates the sample 42, and fluorescent radiation is passed through the optics and polarizer 44 to the detector 46.

In operation, the microprocessor 30 sets the timer/master counter 50 to set the on time for the laser 40, and the laser off counter 52 to determine the time at which the laser 40 is turned off. The microprocessor 30 further sets the window open counter 54 to correspond to the opening of the data acquisition window and sets window closed counter 56 to correspond to the closing of the data acquisition window. A gate 58 receives the output of the detector 46 and passes it to the counter 60 during the data acquisition window. Control for the gate 58 comes from the window open counter 54, which permits passage of pulses from the detector 46 to the counter 60, and the window closed counter 56 which closes the gate 58, precluding data from passing from the detector 46 to the counter 60. Periodically, the value of counts in the counter 60 is transferred under control of the microprocessor 30 to memory 32 for later processing, analysis, and display.

Figure 3:
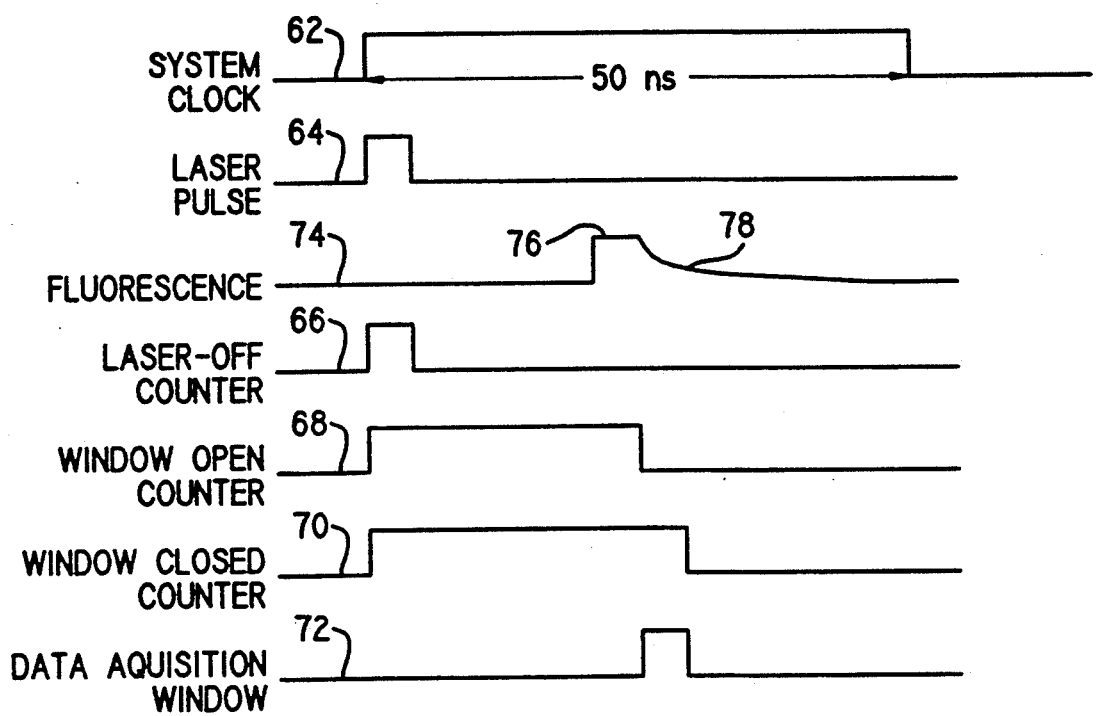
FIG. 3 shows a representative timing diagram for aspects of the time gating system.

FIG. 3 shows the general timing aspects of the circuit of FIG. 2. A system clock 62 provide overall system synchronization and control. An example for the system clock frequency might be 10 MHz. At that frequency the cycle time is 100 ns, giving a maximum 50 ns on period. The laser pulse duration is controlled by the timer/master counter 50 and laser off counter 52. Preferably, the leading edge of the system clock 62 triggers the generation of the laser pulse 64. The trailing edge of the laser pulse is determined by the time set in the laser off counter 52. The waveform 66 of FIG. 3 shows the laser-off counter state, transitioning low when the laser pulse 64 is to terminate. The window open counter pulse 68 runs for a time until the beginning of the data acquisition window 72. The window closed counter pulse 70 runs longer than the window open counter pulse 68, the trailing edge of the window closed counter pulse 70 defining the trailing edge of the data acquisition window pulse 72. The data acquisition window pulse 72 defines the time period in which the data is supplied from the detector 46 (FIG. 2) to the counter 60. The composite fluorescence signal 74 has an initial steady state portion 76 followed by an intensity decay portion 78. In actuality, for any given single laser pulse, it is more probable than not that no photon will be detected for any data acquisition window. Accordingly, the fluorescence signal 74 would be a compilation of events after numerous laser pulses run with various data acquisition window times.

Figure 4:
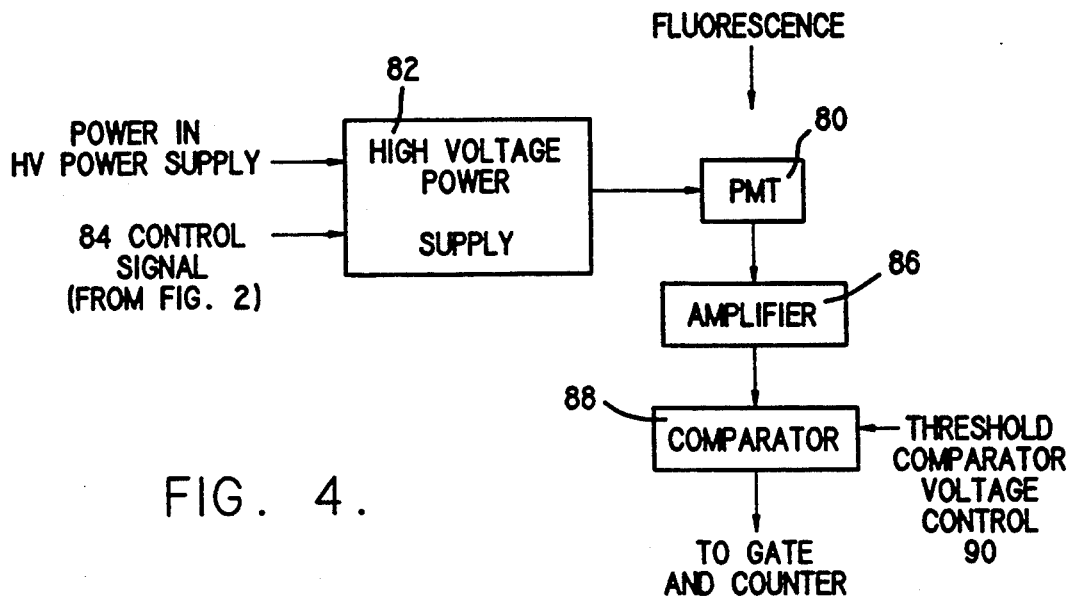
FIG. 4 shows a block diagram detail for the detector printed circuit board for the time gating system.

FIG. 4 shows the detail of the detector PCB 12. Preferably, detection electronics capable of detecting single photon events are used. In the preferred embodiment, a photomultiplier tube ("PMT") 80 is oriented to detect the fluorescence from a sample (not shown). Optimally, the PMT 80 has a low dark current and a high band width, such as 100 MHz. A high voltage power supply 82 supplies power to the PMT 80. A high voltage power supply control signal 84 from the main PCB 14 (shown on FIG. 2) determines the value of high voltage supply from the power supply 82 to the PMT 80. The output of the PMT 80 is amplified as is necessary. Preferably, a comparator 88 allows for selection of the desired pulse amplitude and compensates for offsets in the amplifier 86. The comparator 88 is preferably controlled by a threshold comparator voltage control (from FIG. 2). The output of the comparator 88 goes to the counter 60 (FIG. 2) via gate 58. Preferably, the cable connection from the main PCB 14 to the detector PCB 12 is a 65 ohm shielded ribbon cable whose length is kept less than 12 inches.

Figure 5:
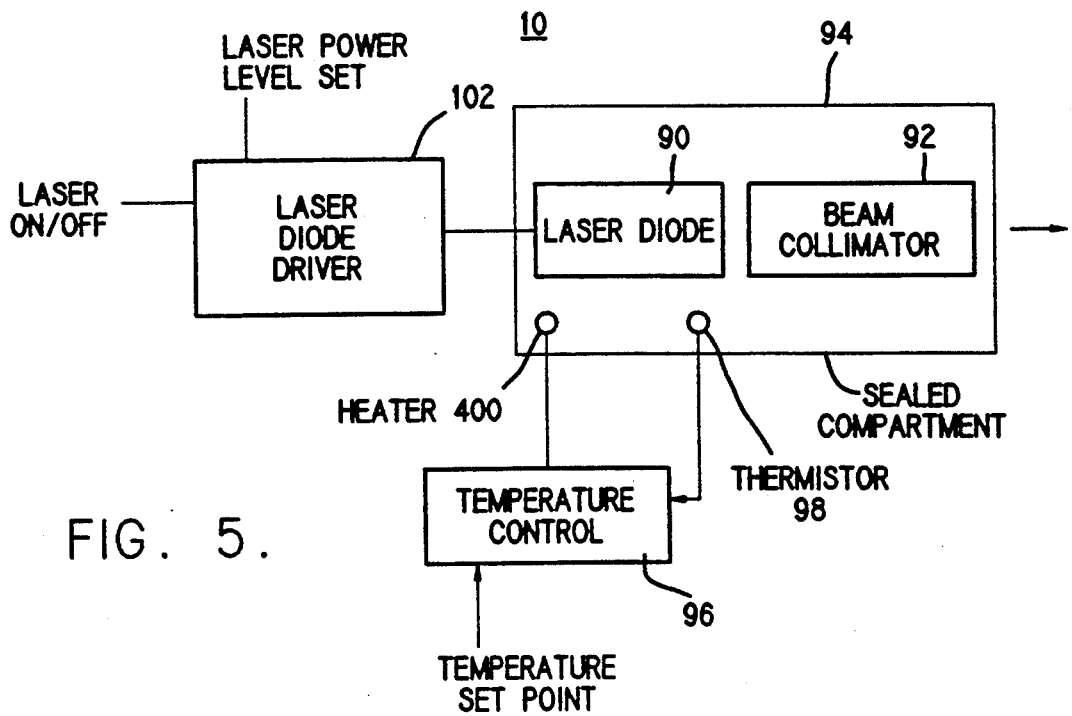
FIG. 5 shows a block diagram detail for the laser printed circuit board in the time gating system.

FIG. 5 shows the detail of the laser PCB 10. Laser diode 90 is preferably housed in a beam collimator 92 and mounted directly on laser PCB 10. For convenience, a socket assembly may be used to ease in changing laser diodes 90. Preferably, the collimator assembly 92 and laser diode 90 are further housed within a sealed compartment 94 with a desiccant (not shown). Temperature control circuit 96 monitors the temperature of the laser diode 90 via a thermistor 98. A heater 100 is controlled by the temperature control 96 to heat the laser diode 90. The temperature set point control (from FIG. 2) determines the temperature at which the temperature control 96 regulates. By varying the temperature of the laser diode 90, tuning of the diode emission wavelength may be made. Generally, the wavelength shifts 0.3 nanometers per degree centigrade. By varying the temperature, the laser wavelength may be changed to the most advantageous wavelength for the particular fluorescable dye. Ordinarily, the laser is operated from 25° C. to 50° C., depending on the particular laser diode and desired wavelength. Optionally, however, the laser may be cooled, using conventional refrigeration techniques. A laser diode driver 102 provides driving power to the laser diode 90. Control inputs to the laser diode driver 102 include the laser on-off control and laser power level set, both of which come from the main PCB 14. Typically, the laser diode 90 is operated at 10 MHz pulse repetition rate and at peak power approximately 6 to 7 times the average rated power output. Exceeding the rated power on a peak basis is possible because the laser pulses are so short that the normal failure mechanism, thermal mirror failure, does not occur since the average power is less than the typical continuous operating power.

Figure 6:
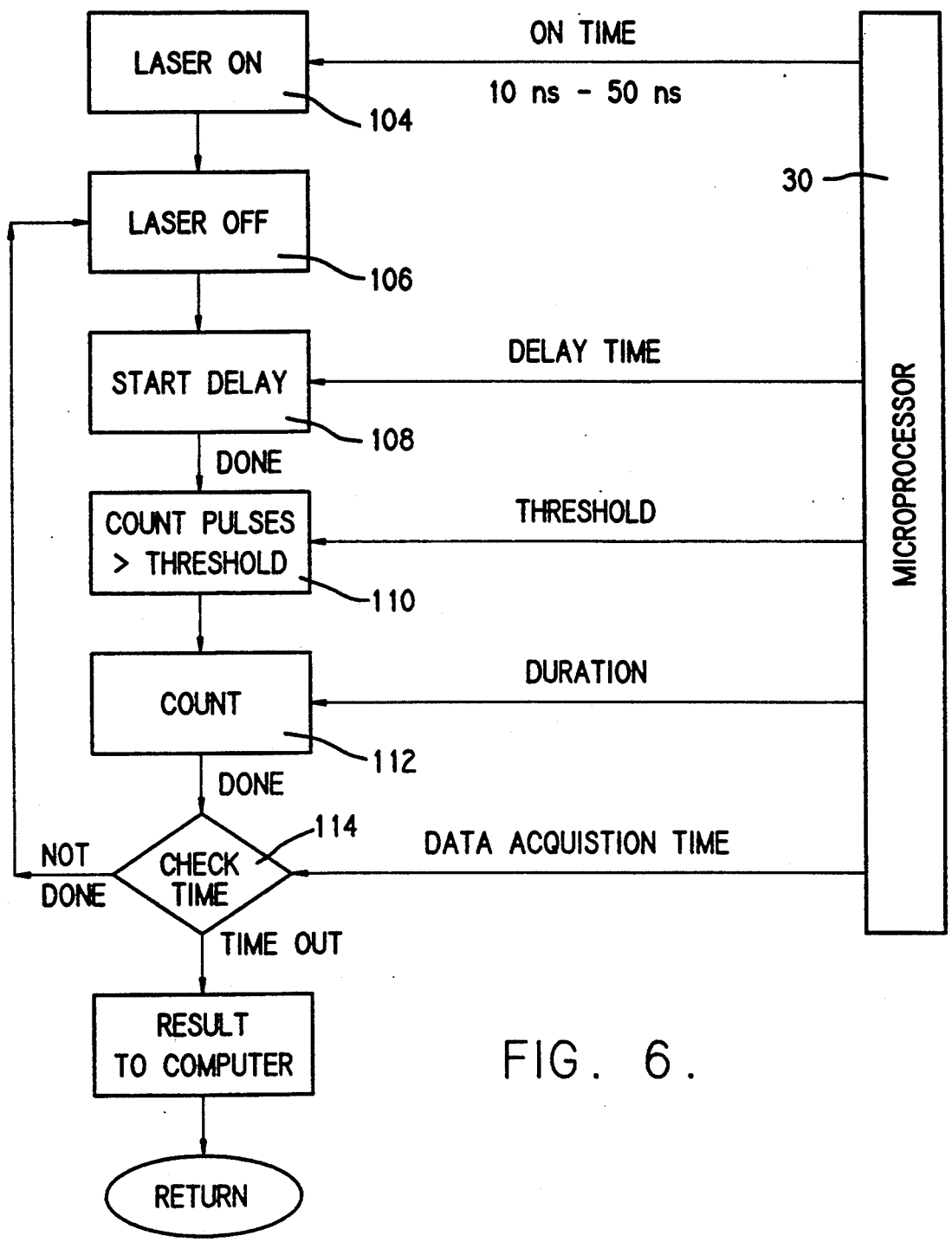
FIG. 6 shows a flow chart for the detection system in the time gating system.

FIG. 6 shows a flow chart for the overall operation. The microprocessor 30 sets the laser on time 104 and laser off time 106. The delay time to the beginning of the data acquisition window is set by the microprocessor 30 and is labeled as start delay 108. Once the data acquisition window opens, pulses exceeding the threshold level as set by the microprocessor 30 are counted at step 110. These events are summed as count 112. If the time for data acquisition has not expired, the decisional block 114 directs the re-initiation of the cycle, causing another laser pulse and counting to begin. When the decision block 114 indicates that the data acquisition time is complete, the results are provided to the computer or other data processing device.

By varying the location of the data acquisition window, a histogram of intensity as a function of time may be compiled. Optionally, the data collection and analysis techniques of Dandliker et al, U.S. Pat. No. 4,877,965 are preferably used to further improve the quality of the data.

The timing resolution of the system may be set as precisely as desired. In the preferred embodiment, a timing resolution of 400 picoseconds was selected to permit accurate formation of fluorescent decay times as short as 2 nanoseconds. The data acquisition window is then taken as multiples of the timing resolution value.

Figure 7:
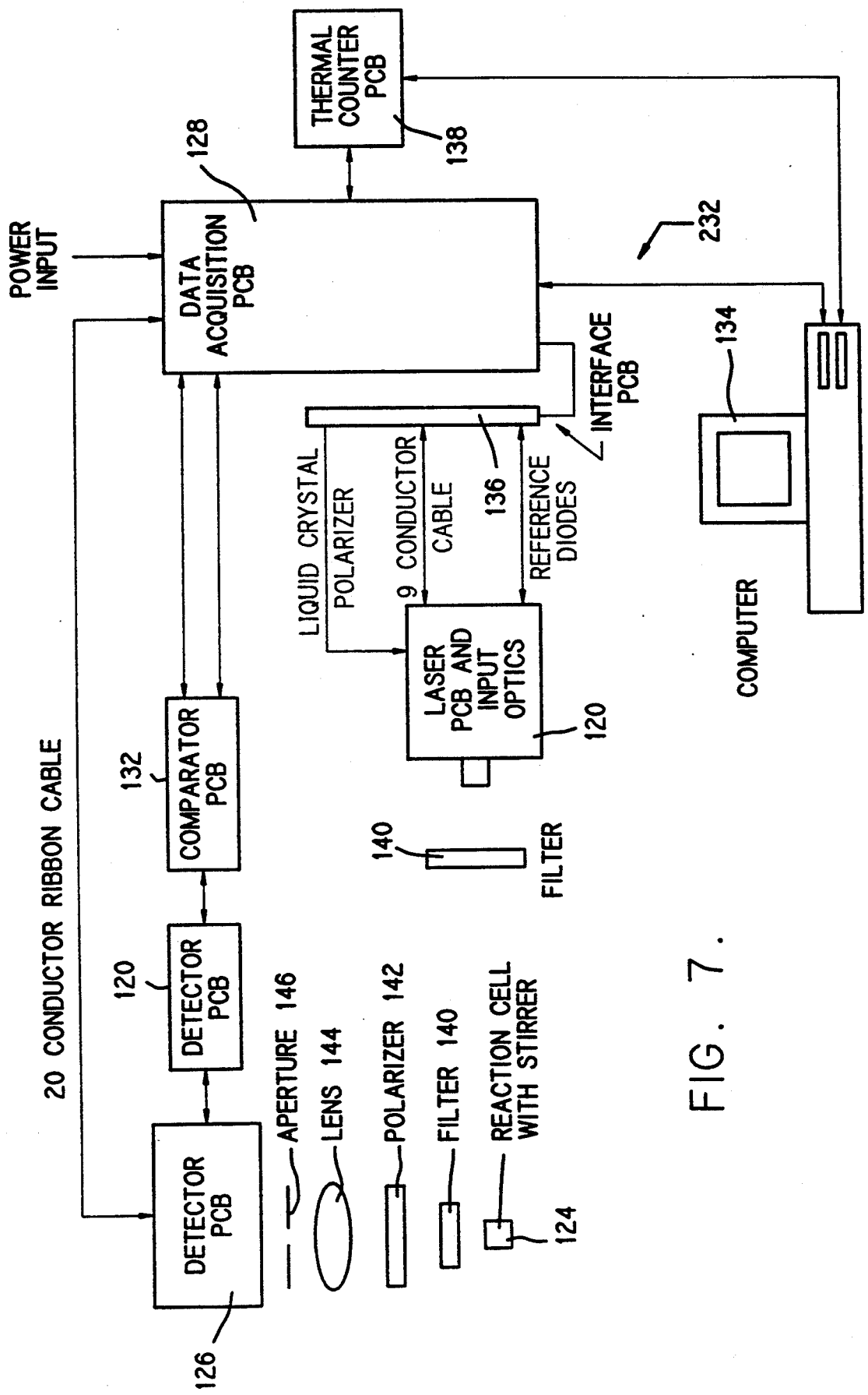
FIG. 7 shows an overview of the fluorometer system for the detection of time of receipt of events.

FIG. 7 shows a systemwide view of a fluorometer in accordance with this invention designed to determine the time of detection of a photon. After numerous repetitions of the detection cycle, a histogram of the number of events as a function of time is developed. In the preferred embodiment, data is collected for time bins, for example, 1,024 time bins or intervals over 75 nanoseconds results in a bin width of 75 picoseconds. A laser PCB and input optics board 120 generates and directs a laser beam towards a reaction cell 124. Fluorescent light from the reaction cell 124 is detected by the detector PCB 126, whose output is amplified by the amplifier PCB 130, whose signal in turn is supplied to the comparator PCB 132, with the ultimate result being supplied to the data acquisition PCB 128. The result from the data acquisition PCB 128 may be provided to a computer 134 or other functionally similar data processing device. Optionally, an interface PCB 136 provides connection between the data acquisition PCB 128 and the laser PCB 120. Further, a thermal control PCB 138 monitors and controls the temperature of the laser diode (not shown). Additionally, optional filters 140, polarizer 142, lens 144, and aperture 146 may be used as known to those skilled in the art and described previously in connection with the embodiment described above.

In operation, the laser PCB 120 provides a sequence of laser pulses to the reaction cell 124. The detector PCB 126 detects receipt of photons, if any, and after amplified by amplifier PCB 130, for the signal which exceeds the level set for the comparator PCB 132, an event is considered detected by the data acquisition PCB 128. Broadly speaking, the detection of an event is then used in two ways. First, a running count of the total number of events is made for the time period of interest. In a preferred embodiment, the time period of interest runs continuously during the detection period. Secondly, the detection of an event is used to determine the time at which the event occurred.

Figure 8:
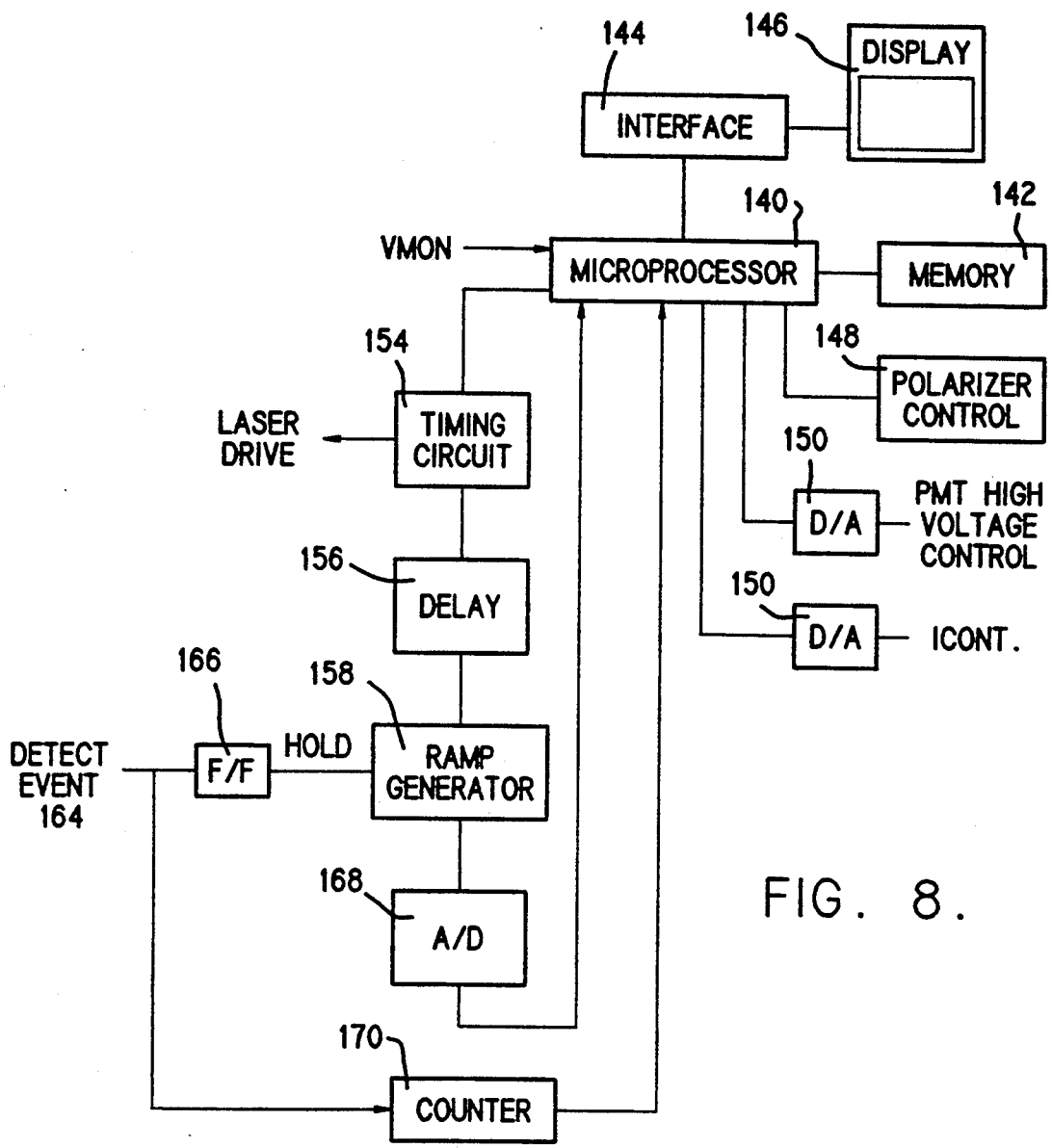
FIG. 8 shows the block diagram detail for the data acquisition processor board for the time of detection system.
Figure 9:
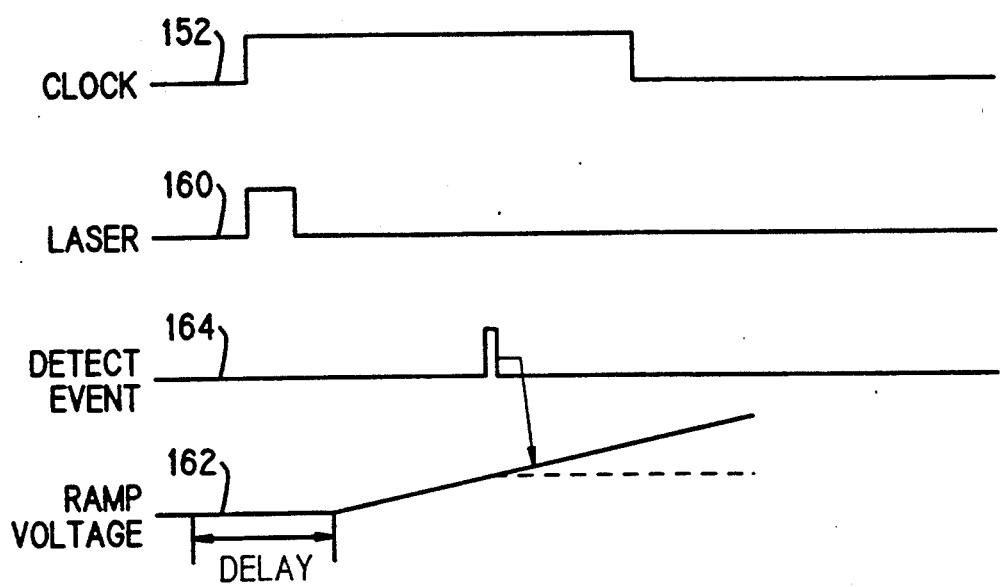
FIG. 9 shows a timing diagram for the time of detection system.

Refer to FIGS. 8 and 9 for a more detailed understanding of the apparatus and methods utilized herein. The microprocessor 140 and memory 42 operate on the data acquisition PCB 128 to control the system. Preferably, an interface 144, such as an RS 232 port, permits connection with a computer 146 or other data processing or display device. The microprocessor 140 provides numerous control signals, such as: control to the polarizer control 128, the PMT high voltage control, and the ICONT signal, typically via digital to analog convertors 150.

An overall clock signal 152 is preferably on the order of 10 MHz. This provides a 100 nanosecond cycle time. The timing circuit 154 generates a laser drive pulse 156 which causes generation of the laser pulse having a shape 160. The timing circuit 154 further causes activation of a delay circuit 156 which in turn, after a predetermined delay, activates ramp generator 158. The ramp voltage 162 begins with a period of delay (see FIG. 9) and then begins a ramp portion. In a preferred embodiment, the delay period is 25 nanoseconds. Upon receipt of a detect event signal 164, the value of the ramp voltage 162 is latched, such as by flip-flop 166. The latched value of voltage from the ramp generator 158 is converted in an analog to digital converter 168 and provided to microprocessor 140 for storage in memory 142. Additionally, the detect event signal 164 is provided to counter 170 which maintains a running count of all detected events.

In the preferred embodiment, the counter 170 counts all events detected, no matter when in the cycle they are detected. Specifically, the counter 170 counts detected events whether during the dark current period, during the laser pulse time, or during the transient state fluorescent decay period. Alternatively, the counter 170 may be activated only during desired times, for example, being inactivated during the dark current time.

In operation, when a detected event 164 is received by the data acquisition PCB 128 (FIG. 8), a certain amount of time is required to determine the time of the detected event, process it, and store it. While this process is ongoing, the time detection system ignores new photons or events until the previously received photon time has been completed. Depending upon the particular hardware chosen, the time during which new photons are ignored can be on the order of 30 microseconds. If the clock frequency is 10 MHz, approximately 300 laser pulses are ignored. Generally, this is insignificant in all but the highest concentration of fluorophores. At nominal concentrations, typical input rates of photon events from the PMT is approximately 10,000 per second. Accordingly, a photon is detected roughly every 1,000 pulses. For higher concentration of fluorophore, pulse rates may increase by orders of magnitude. To maintain linearity, laser diode peak power may be lowered or apertures may be placed in the detection path. Alternatively, for larger pulse rates, the counter 170 monitors all detected events, independent of the timing of the detected event.

Through this method, the shape of the histogram may be determined by measuring the time of the detected event for a large number of samples. However, because certain events may be ignored during the processing time, the counter 170 provides for the calculation of a scale factor so as to provide a true measure of the intensity of the fluorophore decay as a function of time. In the preferred method, the dark current signal level (the level of current or detected events existing even with no laser pulse or fluorescent decay) is detected. Next, the value of the dark current is subtracted from the total number of counts in each bin. In this way, a true measure of the number of detected events occurring during that time bin is set. Next, the total number of counts in the time bins are summed, giving a measure of the total number of events detected. Next, the ratio of events counted by counter 170 and the number of events found by integrating all of the bin counts (less the dark current) is multiplied times the value in each bin. In this way, compensation is made for events which occurred during the analysis, as indicated by a detected event stored by counter 170, but which did not form part of the histogram as detected by the sampling of values from the ramp voltage 162 (presumably because an event was being processed).

It is necessary to give equal weight to detection of events for all time bins. If the system were to always record the first detected event after the laser pulse, for example, a disproportionate number of events would be detected early in the histogram, thereby skewing the histogram results. One method for avoiding such skew in the histogram is to provide for a random starting time for detection. In the preferred embodiment, this time is determined by re-enabling the ability to measure the ramp voltage 160 to any time directly following storage of the preceding event. In this way, no down time is suffered, and, given the relatively long period of time for data acquisition and storage, the exact time of resumption of monitoring for a subsequent detected event is essentially random.

Figure 10:
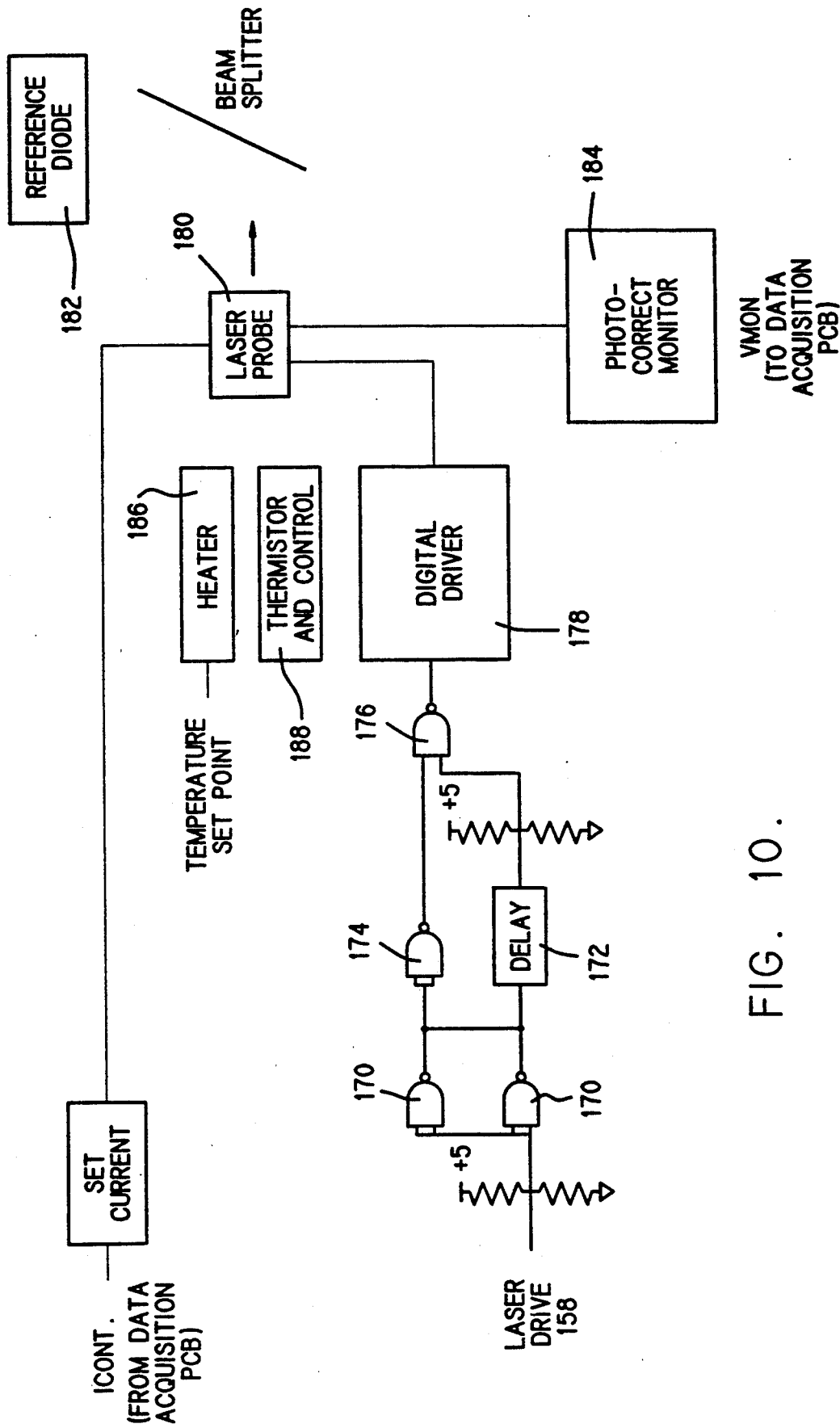
FIG. 10 shows a detailed block diagram for the laser PCB of the time of detection system.

A detailed block diagram for the laser PCB 120 is provided in FIG. 10. The laser PCB 120 takes the laser drive pulse 158 from the data acquisition processor board (FIG. 8) and generates a laser light pulse. In a preferred embodiment, the duration of the pulse is on the order of a few nanoseconds, and is of relatively high power. An incoming rising edge in the laser drive pulse 158 causes generation of a laser flash. Input logic 170, 174, and 176 generate a very sharp rising edge, which is supplied to the high-powered digital driver 178. The digital driver 178 provides power to the laser diode 180. The current used by the laser diode 180 is set by the signal ICONT from the data acquisition PCB (FIG. 8). The duration of the laser pulse may be varied by changing the delay 172. Further, the amplitude of the laser pulse is varied by setting the current value ICONT. A reference diode 182 monitors the long term stability of the laser output. Preferably, the reference diode 182 is located downstream of the optics and filter through which the laser beam passes. In this way, the total input power directed to the sample may be monitored. Various factors which affect total input power would include laser performance or degradation, cleanliness of the optical components or degradation of the laser filter. A photocurrent monitor 184 monitors the photocurrent of the laser diode 180. Since the pulse length and repetition rate are known, the average power being generated by the laser diode 180 may be calculated. This power reading, labeled VMON, is fed back to the data acquisition PCB (FIG. 8).

Additionally, an optional heater 186 and thermistor and temperature control 188 provide temperature control to the laser diode 180. The temperature set point is provided from the data acquisition PCB to the heater 186 and control 188. As described in connection with the first embodiment, varying the temperature changes the wavelength of the laser diode 180.

Figure 11:
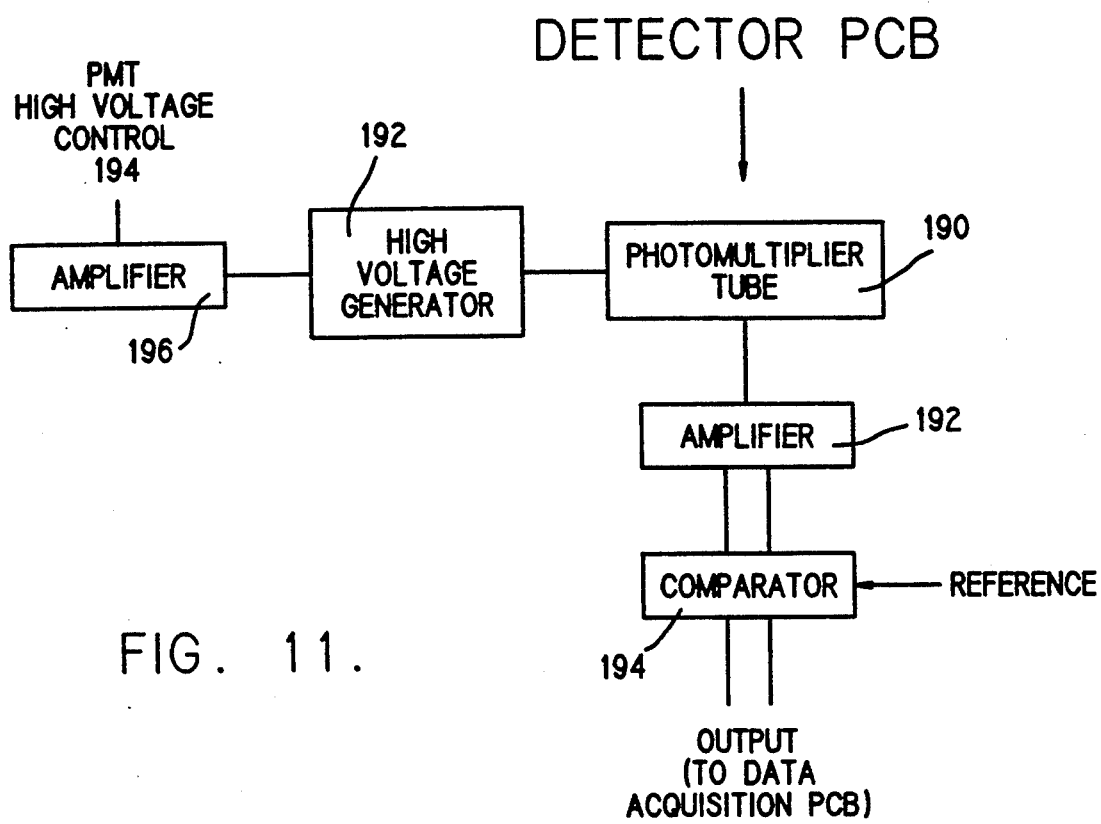
FIG. 11 shows a detailed block diagram of the detector printed circuit board for the time of detection system.

The detector PCB 126 is described in detail in FIG. 11. The photomultiplier tube 190 receives fluorescent radiation from the sample. A high voltage generator 192, under control the PMT high voltage control signal 194 as amplified 196 provides high voltage to the PMT 190. The output of the PMT 190 is passed through amplifier 192 and sent through comparator 194. If the detected and amplified value exceeds the reference value, the comparator passes the signal as output to the data acquisition PCB. Preferably, the amplifier 192 is connected to the comparator 194 by dual coaxial cable providing a differential signal. The comparator 194 is similarly connected via coaxial cables to the data acquisition PCB.

Figure 12:
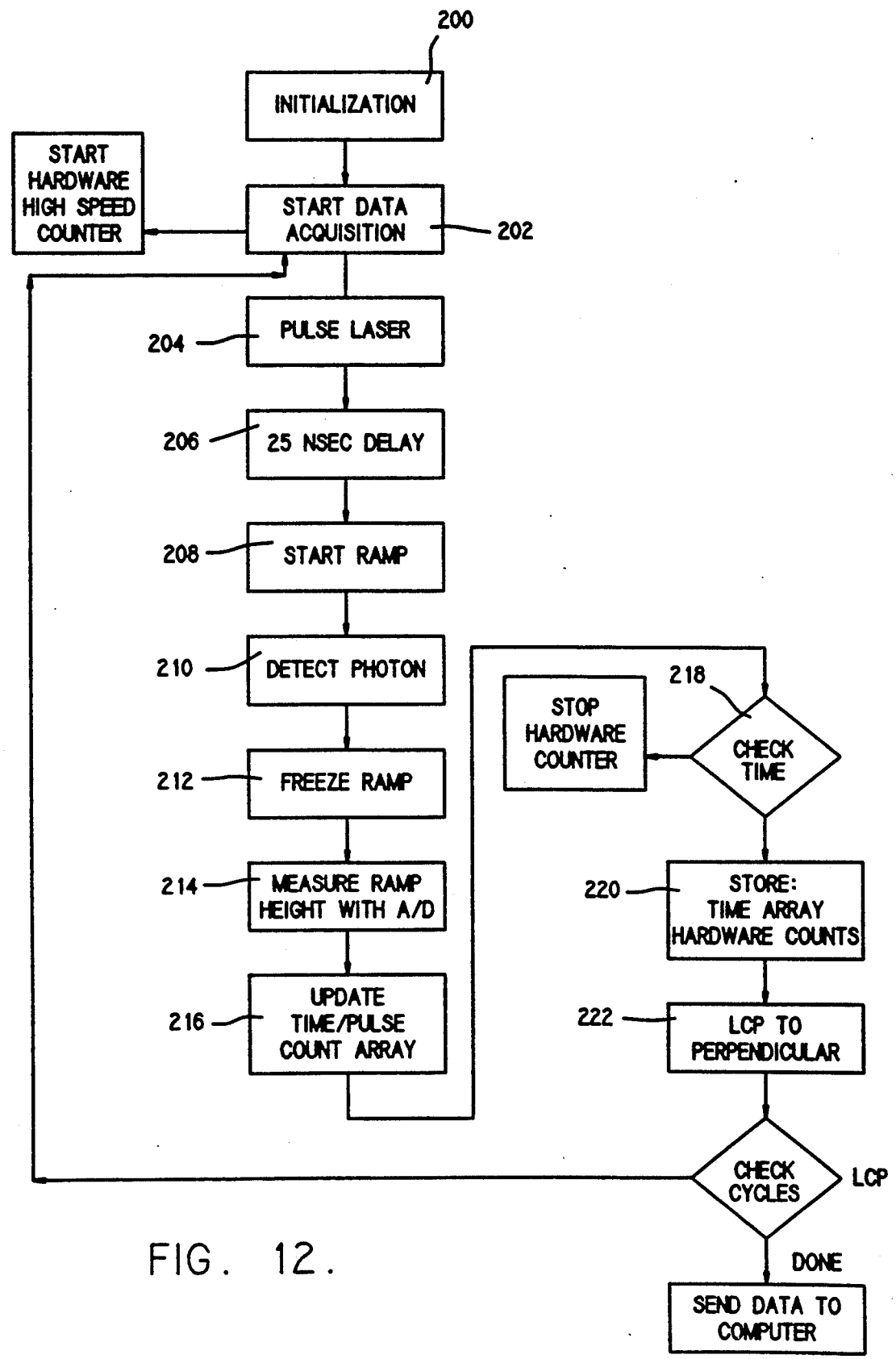
FIG. 12 is a flow chart for operation of the detection system for the time of detection system.

FIG. 12 shows a flow chart for the preferred method of operation. During the initialization phase 200, the following items are set: the PMT voltage, laser intensity, data acquisition time, liquid crystal polarizer ("LCP") cycles, and LCP to parallel. Next, data acquisition starts 202. After the laser pulse 204 and a delay 206, the ramp 208 begins. If a photon is detected 210, the ramp voltage is frozen 212 and the height measured and converted to digital 214. The data updates 216 the appropriate bin. If the data acquisition time decision 218 exceeds the allowed time, the hardware counter is stopped. If data acquisition time remains, the laser pulse sequence is begun again. When data acquisition time is completed, the data from the counter is stored 220. Optionally, the polarizer may be changed to the other orientation instead 222.

EXPERIMENTAL RESULTS

The devices and methods described herein have been utilized with fluorescence measurements from numerous systems, especially biological systems. The data reported herein were generated with the time of detection system.

The fluorometry system described herein when used in conjunction with the fluorescable dyes described in copending applications to Arrhenius and Dandliker and Hsu result in an improvement in signal detection of over 100 times over conventional techniques. The following table lists the detectable concentration level of dye at the point where the intensity of the desired signal equals the intensity of the background. The buffer used contains 1% bovine serum albumin. The data are as follows:

TABLE 1

| Wavelength | Mode | Concentration |
| --- | --- | --- |
| 490 nm | Steady-state | $1.5 \times 10^{-9}$ |
| 685 nm | Steady-state | $2.2 \times 10^{-10}$ |
| 685 nm | Transient-state | $1.1 \times 10^{-11}$ |

By selecting a dye with a longer wavelength and by utilizing time gating and the time of detection techniques described above, a significant improvement in the detected signal intensity is achieved.

Figure 13:
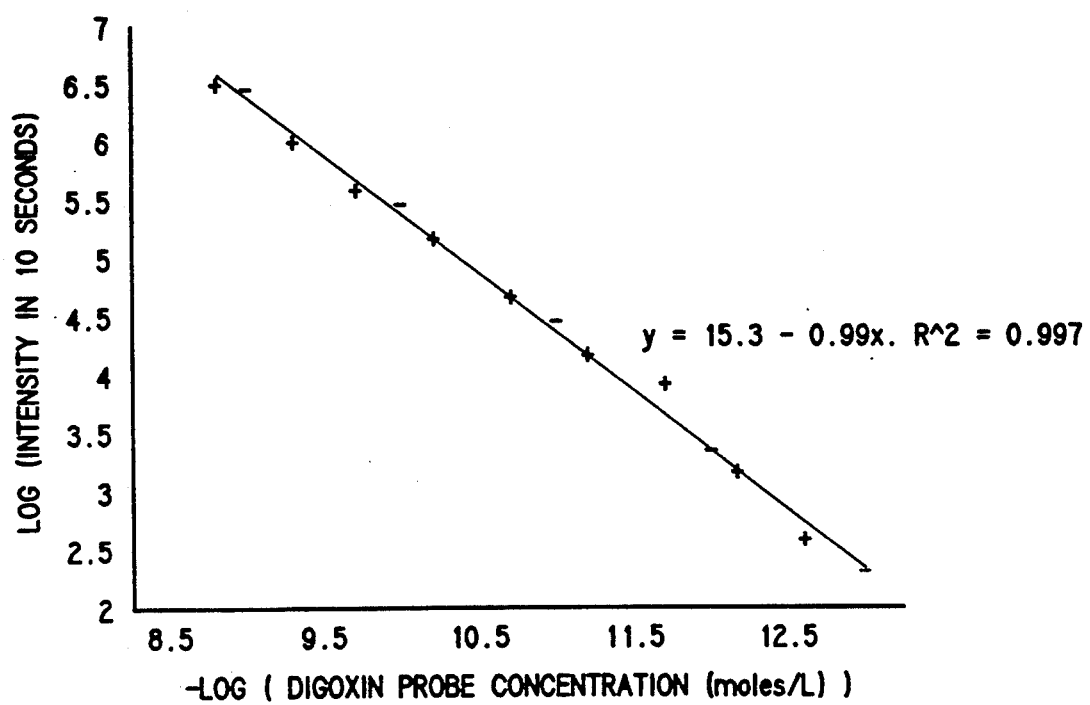
FIG. 13 is a graph showing sensitivity and linearity utilizing the time of detection system showing the log of the intensity of counts as a function of the log of the digoxin probe concentration.

As to linearity, FIG. 13 shows a log-log plot of the intensity as a function of Digoxin probe concentration. The results show the system to be linear over four orders of magnitude. Further, concentrations as low as approximately $10^{-13}$ moles per liter may be detected. An accurate system should have such a linear response, since as the concentration of fluorescable material decreases, there should be a correspondingly linear decrease in the number of counts detected.

Figure 14:
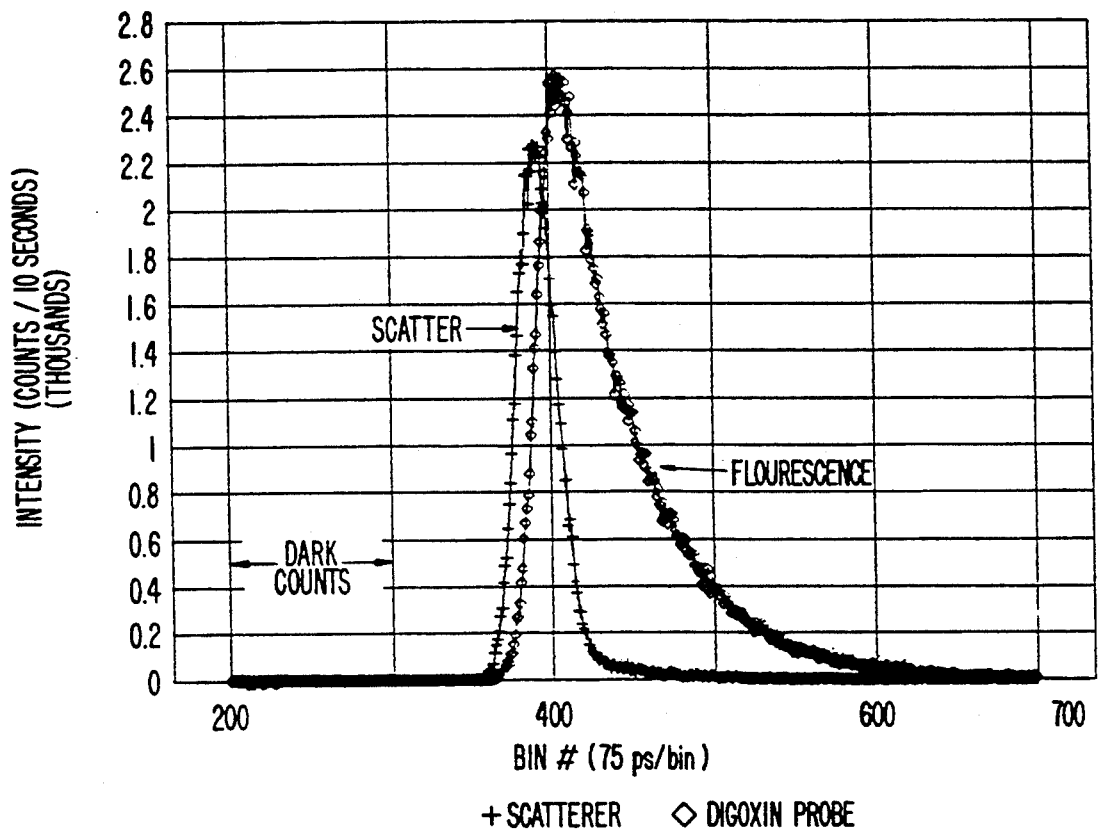
FIG. 14 is a graph showing the digoxin serum assay utilizing the time of detection system, showing the raw data for the scatter and fluorescence curves, with intensity (counts/seconds) in thousands versus the time bin number.

Actual data from a sample is shown in FIG. 14. The intensity (number of counts per 10 seconds) is shown on the y-axis measured in thousands. The x-axis shows the time bin number, with each bin corresponding to a 75 picosecond interval. The scatter curve peaks slightly to the left of the peak of the fluorescence curve. The dark current counts are shown generally in the time from bin number 200 to bin number approximately 300. The decay of the fluorescence curve as a function of time provides a histogram which may be used in conjunction with data analysis techniques such as those disclosed in Dandliker et al. U.S. Pat. No. 4,877,965.

Figure 15:
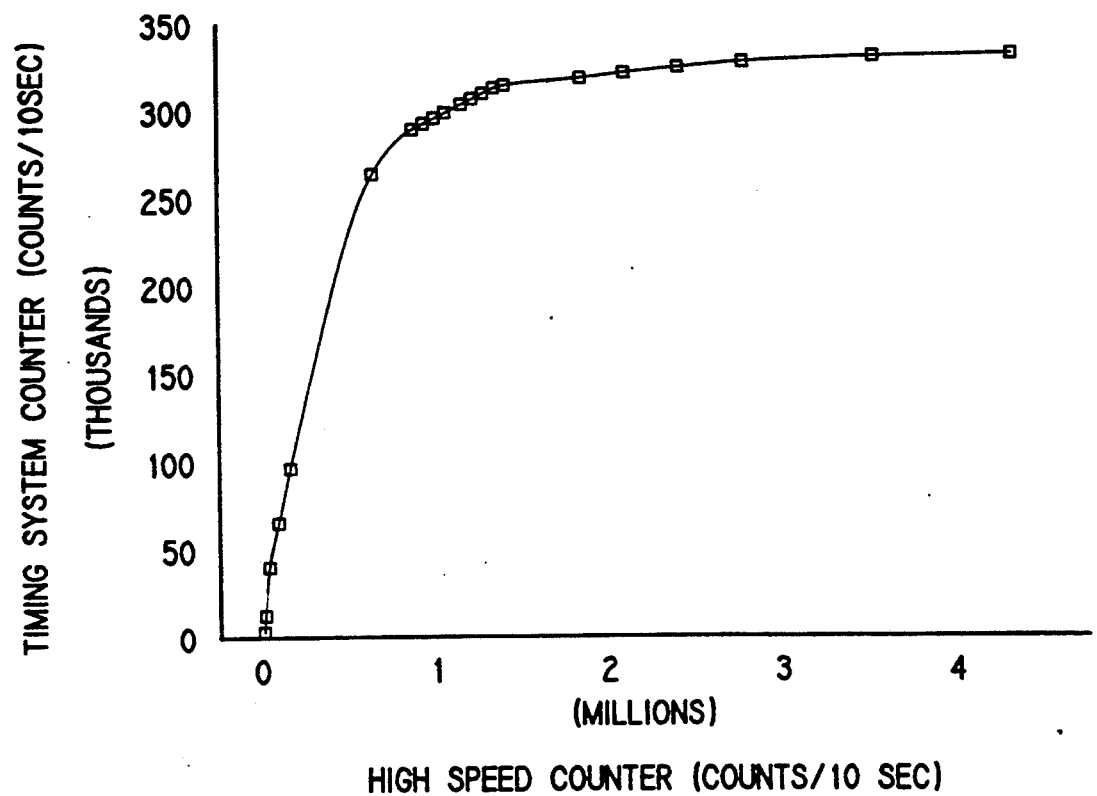
FIG. 15 shows a graph of the timing system counter (counts/10 seconds) in thousands versus the high speed counter (counter/10 seconds) in millions for the time of detection system.

As described in detail above, the time of detection system forms a histogram which accurately depicts the shape of the intensity curve, and then scales that shape to provide an absolute measure of intensity as a function of time. In the preferred embodiment, the method used is to monitor the total number of counts with a high speed hardware counter and to determine the total number of counts comprising the shape histogram by integrating those counts. The histogram shape curve is then multiplied by the ratio of the hardware counts to the total integrated counts. FIG. 15 shows the integrated timing system counts as a function of high speed counter counts. A maximum of 33,000 counts per second may be detected by the timing system counter. This however is a function of the specific hardware chosen. If a dedicated processor or faster processor were chosen, as are design choices available to those skilled in the art, the time required to store a time of receipt of an event is decreased, and accordingly, the number of counts per second may be increased.

Figure 16:
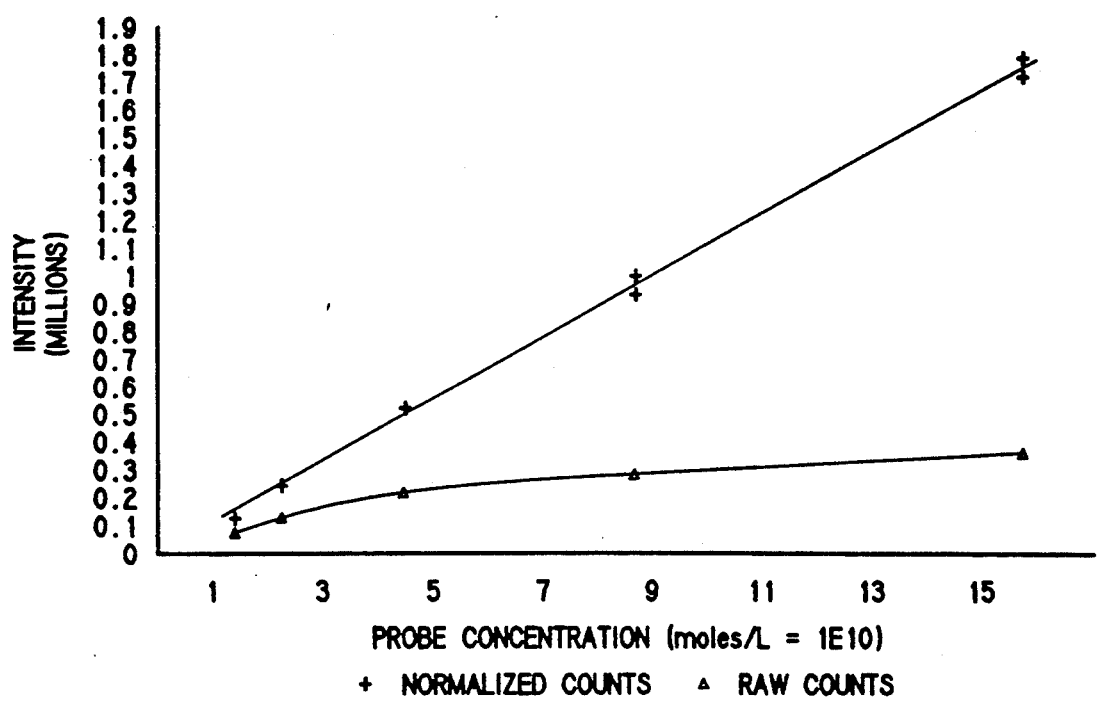
FIG. 16 shows a graph of the raw counts and normalized counts for time of detection system, with intensity in millions versus the probe concentration (moles per liters $\times 10^{10}$.

FIG. 16 shows the intensity (in millions) as a function of probe concentration (in moles per liter $\times 10^{10}$) for two curves. The upper curve shows the normalized counts and the lower curve shows the raw counts. Through use of the techniques described above, the raw counts may be converted into normalized counts, thereby providing linearity of intensity as a function of probe concentration.

In the time of receipt system, the high repetition rates of the laser diode combined with the hardware counter compensation have provided the best useful data. Preferably, the photon flux is relatively low. With a relatively low photon flux, the probability of two photons hitting the PMT at the same time is substantially reduced, thereby avoiding system non-linearity. As the concentration of the fluorophore is decreased, the laser power and/or repetition rate may be increased to speed data acquisition.

Figure 17:
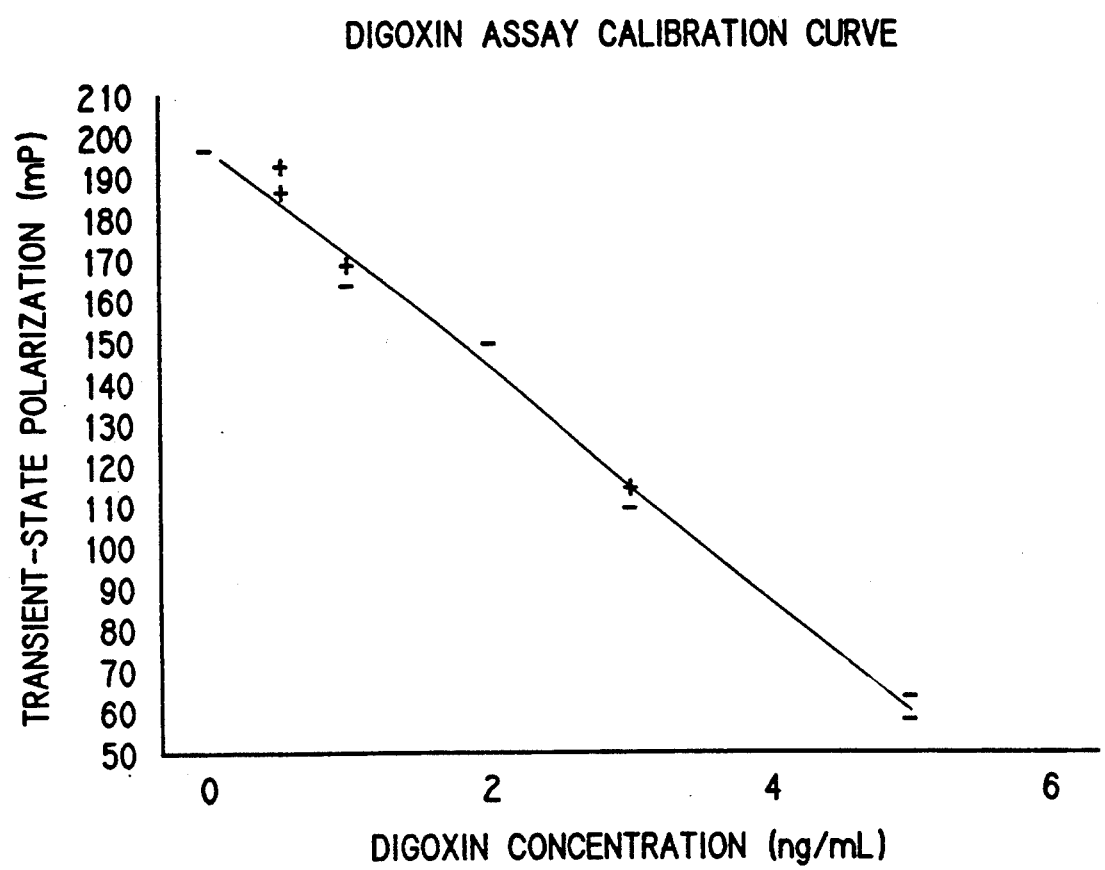
FIG. 17 shows a graph of transient-state polarization versus Digoxin concentration.

FIG. 17 shows a graph of transient-state polarization versus digoxin concentration.

A 20 microliter sample containing known levels of digoxin were incubated with 25 microliters of rabbit antidigoxin antibody for 5 minutes in 100 microliter of buffer. The 20 microliters of fluorescently labelled digoxin probe (at a concentration $5 \times 10^{-11}$M was then added and incubated for an additional 5 minutes. Finally, the solutions were diluted with 1 milliliter of buffer. The fluorescence signal was then read using the time of detection hardware apparatus.

Though the invention has been described with respect to a specific preferred embodiment, many variations and modifications will immediately become apparent to those skilled in the art. It is therefore the intention that the appended claims be interpreted as broadly as possible in view of the prior art to include all such variations and modifications.

We claim:

1. A fluorometer for exciting a sample including a fluorophore and for detecting fluorescent emissions from the sample comprising:
    a laser diode for exciting the sample,
    a detector positioned to receive fluorescent emission, and
    means for determining the time of receipt of the fluorescent emission, said means including a ramp generator.

2. The fluorometer of claim 1 wherein the means for determining the time of receipt of the fluorescent emission further includes a means to sample the ramp.

3. The fluorometer of claim 1 further including a counter operatively connected to receive the output of the detector.

4. The fluorometer of claim 1 detector comprises means for detecting fluorescent emission from a caged dicarboxy silicon phthalocyanine digoxlgenin dye.

5. A method for generating a histogram of the intensity as a function of time for a transient state fluorescence determination comprising the steps of:
    detecting events of fluorescence,
    counting the total number of detected events,
    determining a preliminary histogram of shape of the histogram,
    counting the number of events comprising the preliminary histogram, and
    multiplying the preliminary histogram times the ratio of the count of the total number of events and the count of the number of events comprising the preliminary histogram.

6. The method of claim 5 further including the step of measuring the dark current and subtracting the dark current contribution from the preliminary histogram prior to the counting and multiplication steps.

7. The method for generating a histogram of detected events from an excitation pulse in a transient state fluorometry system comprising the steps of:
    a) monitoring for a detected event,
    b) upon an event, determining the time of occurrence of the detected event,
    c) storing the time determined in step b and ignoring for purposes of step b other detected events while performing this step,
    d) upon completion of step c, resume monitoring at step a at a time after completion of step c not related to the time of the excitation pulse, and
    e) generating a histogram using the times stored in step c.

8. The method of claim 7 wherein in step d, the monitoring at step a is measured immediately after completion of step c.

9. The method of claim 2 wherein the time after completion of step c is a random time.

10. A method for generating a histogram of detected events in the transient state fluorometry system comprising the steps of:
    a) monitoring for a detected event,
    b) upon an event, determining the time of occurrence of the detected event by sampling a ramp voltage,
    c) storing the time determined in step b and ignoring for purposes of step b other detected events while performing this step,
    d) upon completion of step c, resume monitoring at step a at a time after completion of step c and,
    e) generating a histogram using the times stored in step c.

11. The method of claim 10 wherein after the ramp voltage is sampled, the voltage is converted to a digital representation.

12. A fluorometer for exciting a sample including a fluorophore and for detecting fluorescent emissions from the sample comprising:
    a laser diode for exciting the sample,
    a detector positioned to receive fluorescent emission, and means for determining the time of receipt of the fluorescent emission, said means including a delay generator.

13. The fluorometer of claim 12 further including means for ignoring the decay fluorescence and background occurring during and immediately after the excitation by the laser diode.

14. The fluorometer of claim 13 wherein time gating is used to exclude the decay fluorescence and background immediately after the pulse of radiation.

15. The fluorometer of claim 12 further including a counter operatively connected to the detector to receive the output of the detector.

16. The fluorometer of claim 15 further including a time gate generator.

17. The fluorometer of claim 16 wherein the time gate generator gates the output of the detector.

18. The fluorometer of claim 16 which further includes a gate which receives as input the output of the detector and is controlled by the output of the time gate generator.

19. The fluorometer of claim 16 wherein the time gate generator includes a counter.

20. The fluorometer of claim 19 wherein the time gate generator includes a window open counter and a window closed counter.

21. The fluorometer system of claim 15 wherein the detector is a photomultiplier tube.

22. The fluorometer of claim 15 wherein the detector is red sensitive.

23. The fluorometer of claim 15 wherein the detector is infrared sensitive.

24. The fluorometer of claim 15 wherein the laser diode is rotatable relative to the sample.

25. The fluorometer of claim 15 wherein the laser diode radiates in the red to infrared range.

26. The fluorometer of claim 15 wherein the laser diode has a variable wavelength.

27. The fluorometer of claim 26 further including a temperature variation device.

28. The fluorometer of claim 26 wherein the laser diode is a tunable laser diode.

29. The fluorometer of claim 28 wherein the laser diode is a quantum well laser diode.

30. The fluorometer of claim 15 further including optics.

31. The fluorometer of claim 15 further including a display.

32. The fluorometer of claim 12 wherein the detector comprises means for detecting fluorescent emission from a caged dicarboxy silicon phthalocyanine digoxigenin dye.

* * * * *